United States Patent [19]

Harada et al.

[11] Patent Number: 5,098,775
[45] Date of Patent: Mar. 24, 1992

[54] BODY FLUID-ABSORBING ARTICLE

[75] Inventors: Nobuyuki Harada, Suita; Yoshihiro Motono, Himeji; Kazumasa Kimura, Ikoma; Tadao Shimomura, Toyonaka, all of Japan

[73] Assignee: Nippon Shokubai Kagaku Kogyo Co., Ltd., Osaka, Japan

[21] Appl. No.: 498,846

[22] Filed: Mar. 26, 1990

[30] Foreign Application Priority Data

Mar. 29, 1989 [JP] Japan .................... 1-75071
Apr. 27, 1989 [JP] Japan ................... 1-105988

[51] Int. Cl.$^5$ ............... A61F 13/15; A61F 13/20; D04H 1/08; B32B 27/34
[52] U.S. Cl. ........................... 428/281; 428/280; 428/282; 428/283; 428/284; 428/287; 428/290; 604/367; 604/368; 604/378; 604/379
[58] Field of Search ........... 428/283, 284, 287, 290, 428/281, 282; 604/379, 367, 368, 378

[56] References Cited

U.S. PATENT DOCUMENTS

| | | | |
|---|---|---|---|
| 4,604,313 | 8/1986 | McFarland et al. | 428/283 |
| 4,721,647 | 1/1988 | Nakanishi et al. | 428/283 |
| 4,822,668 | 4/1989 | Tanaka et al. | 428/283 |
| 4,857,065 | 8/1989 | Seal | 428/283 |

FOREIGN PATENT DOCUMENTS

| | | |
|---|---|---|
| 0202125 | 5/1986 | European Pat. Off. . |
| 0304952 | 8/1988 | European Pat. Off. . |
| 62-170247 | 7/1987 | Japan . |

OTHER PUBLICATIONS

European Search Report 90 30 325, Jun. 26, 1991.

*Primary Examiner*—George F. Lesmes
*Assistant Examiner*—James D. Withers
*Attorney, Agent, or Firm*—Omri M. Behr

[57] ABSTRACT

In a body fluid-absorbing article composed of a liquid-permeable front-surface member, a liquid-impermeable rear-surface member, and a fibrous absorbent member nipped therebetween and adapted to be used with the front-surface member held in contact with the human body, by the improvement having disposed in half of the thickness of the absorbent member on the front-surface member side an absorbent composite (A) obtained by applying an ethylenically unsaturated monomer capable of forming an absorbent polymer by polymerization or an aqueous solution of the monomer to a fibrous web and thereafter polymerizing the monomer.

15 Claims, 1 Drawing Sheet

BODY FLUID-ABSORBING ARTICLE

BACKGROUND OF THE INVENTION

1. Field of the Invention

This invention relates to a body fluid-absorbing article. More particularly, it relates to a body fluid-absorbing article which possesses a highly satisfactory ability to absorb and retain body fluid and a notably improved capacity for absorption enough to give comfort to the user and, therefore, finds utility in such sanitary articles as disposable diapers and sanitary napkins.

2. Description of the Prior Art

In recent years, in the field of body fluid-absorbing articles such as disposable diapers and sanitary napkins, those using so-called absorbent polymers as an absorbent medium have come to find general acceptance. Since these absorbent polymers are generally in the powdery form, they are fixed in the absorbent media of body fluid-absorbing articles as nipped between sheet-like substrates of fibrous pulp or paper or as incorporated in fibrous pulp. In the body fluid-absorbing articles using the absorbent polymers in the manner described above, there arises the problem of leakage because the absorbent polymers are fixed so infirmly that the absorbent polymer gels produced after absorption of body fluid are suffered to gather locally or slide out of place.

Recently, to take the place of such powdery absorbent polymers and body fluid-absorbing articles using such absorbent polymers, an absorbent composite obtained by applying to a substrate a water-soluble monomer capable of being converted into an absorbent polymer and subsequently polymerizing the monomer (Japanese Patent Laid-Open SHO 57(1982)-500,546 and Japanese Patent Laid-Open SHO 60(1985)-149,609) and a body fluid-absorbing article using this absorbent composite as an absorbent medium (Japanese Patent Laid-Open SHO 62(1987)-170,247) have been proposed. Though the body fluid-absorbing articles using this absorbent composite are capable of preventing the absorbent polymer gels resulting from the absorption of body fluid from the unwanted movement, they are incapable of fully manifesting the ability of absorption of the absorbent component, highly uneconomical, and unsatisfactory in terms of capacity for absorption.

An object of this invention, therefore, is to provide a novel body fluid-absorbing article.

Another object of the present invention is to provide a body fluid-absorbing article which has no possibility of entailing the unwanted movement of an absorbent polymer gel produced in consequence of absorption of such body fluid as urine or menstruation and possesses an outstanding ability to absorb and retain the body fluid

SUMMARY OF THE INVENTION

The objects described above are accomplished in a body fluid-absorbing article composed of a liquid-permeable front-surface member, a liquid-impermeable rear-surface member, and a fibrous absorbent member nipped therebetween and adapted to be used with the front-surface member held in contact with the human body, by the improvement having disposed in half of the thickness of the absorbent member on the front-surface member side an absorbent composite (A) obtained by applying an ethylenically unsaturated monomer capable of forming an absorbent polymer by polymerization or an aqueous solution of the monomer to a fibrous web and thereafter polymerizing the monomer.

These objects are further accomplished, in a body fluid-absorbing article composed of a liquid-permeable front-surface member, a liquid-impermeable rear-surface member, and a fibrous absorbent member nipped therebetween and adapted to be used with the front-surface member held in contact with the human body, by the improvement having disposed in half of the thickness of the absorbent member on the front-surface member side an absorbent composite (A) obtained by applying an ethylenically unsaturated monomer capable of forming an absorbent polymer by polymerization or an aqueous solution of the monomer to a fibrous web and thereafter polymerizing the monomer and having disposed in half of the thickness of the absorbent member on the rear-surface member side a powdery absorbent polymer (B).

In accordance with this invention, the objects described above are accomplished by causing a specific absorbent composite having an absorbent polymer integrated with a fibrous web and optionally a powdery absorbent polymer to be disposed at specific positions within an absorbent member of a body fluid-absorbing article thereby enabling the absorbent composite and the powdery absorbent polymer to manifest effectively the body fluid-absorbing ability inherently possessed thereby.

Owing to the simple construction having the absorbent composite disposed in half of the thickness of the absorbent member on the front-surface side and optionally the powdery absorbent polymer disposed in half of the thickness of the absorbent member on the rear-surface side, the body fluid-absorbing article of this invention is enabled to manifest the following conspicuous effects.

(a) Since the body fluid is efficiently absorbed and retained by the absorbent composite, the absorption of the body fluid occurs at a high speed and the amount of the absorbed body fluid suffered to return to the surface under the load of the body weight is extremely small. The body fluid-absorbing article, therefore, gives a comfort to the user and prevents the user's skin from mustiness and rash.

(b) Since the absorbent polymer is integrated with the fibrous web in the absorbent composite, the absorbent polymer gel which occurs after absorption of body fluid does not move out of position. Moreover, the absorbent member in the wet form retains high strength enough to preclude otherwise possible deformation.

(c) Since the body fluid is efficiently absorbed by the absorbent composite and it is retained amply and strongly by the powdery absorbent polymer, the absorption of the body fluid occurs at a high speed and in a large volume and the amount of the absorbed body fluid suffered to return to the surface under the load of the body weight is extremely small. The body fluid-absorbing article, therefore, gives a comfort to the user and prevents the user's skin from mustiness and rash.

(d) Since the powdery absorbent polymer is isolated from the wearer's body by the absorbent composite and the absorbent composite which has absorbed the body fluid while the body fluid-absorbing article is in use prevents the powdery absorbent polymer gel from unwanted movement, the absorbent member in the wet state retains high strength enough to avoid deformation in spite of the incorporation therein of the powdery absorbent polymer.

BRIEF DESCRIPTION OF THE DRAWINGS

The preferred embodiments of the present invention may be illustrated and elucidated by the following figures.

EXPLANATION OF THE PREFERRED EMBODIMENT

Figure 1:
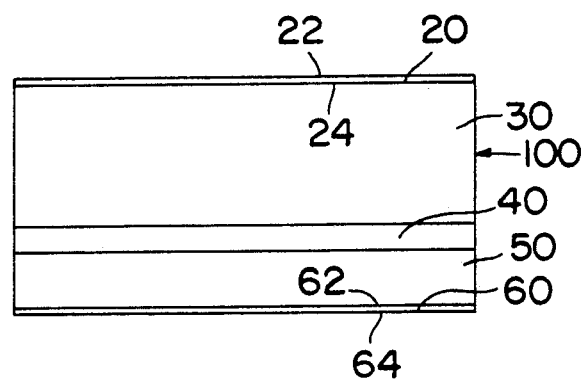
FIG. 1 is an elevational cross-sectional view of an article of Example 1.

The preferred embodiments of the present invention may be described by reference to the drawings. FIG. 1 shows the embodiment produced by Example 1 hereof. The article 10 comprises a rear surface member of polyethylene film 20 having a rear surface 22 and an inward surface 24. Contacting inward surface 24 is fibrous pulp layer 30 which is, on its forward side, contacted by absorbent composite 40. On the other side of said absorbent composite 40 is a further fibrous layer 50 covered by a front surface member 60 of non-woven polyester fabric having an inward surface 62 and a front surface 64. The aforesaid fibrous pulp segments 30 and 50 are so provided that the absorbent composite layer 40 is out of contact with said rear surface and said frontsurface member.

Figure 2:
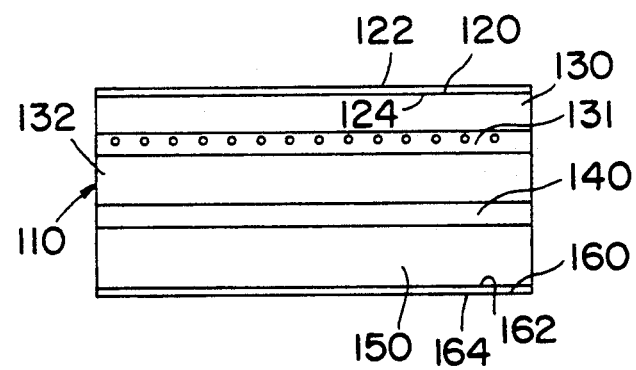
FIG. 2 is an elevational cross-sectional view of an article of Example 7.

A further embodiment as illustrated by FIG. 2 comprises an additional fibrous pulp layer and an interstitial powdery absorbent segment.

In this embodiment, as previously, the rear of the device comprises a rear surface member of polyethylene film 120 having a rear surface 122 and an inner surface 124. The latter contacting a first fibrous pulp layer 130. The other surface of said fibrous pulp layer has absorbed thereon the powdery absorbent polymer 131. A further fibrous pulp layer 132 contacts said powdery absorbent polymer segment 131. The other surface of said fibrous pulp 132 is contacted with said absorbent composite 140 which, as previously, is faced with fibrous pulp layer 150 which is contained by a front surface member 160 of non-woven fabric of polyester 160 having an inner surface 161 in contact with said fibrous pulp and a front surface 164.

The absorbent composite (A) to be used in the present invention is formed by the integration of an absorbent polymer with a fibrous web. Specifically, it is obtained by applying an ethylenically unsaturated monomer capable of forming an absorbent polymer by polymerization or an aqueous solution thereof to a fibrous web by impregnation, spraying, or spreading and thereafter polymerizing the monomer in situ.

The ethylenically unsaturated monomer has no particular restriction except for the requirement that it should be a water-soluble monomer capable of being converted into an absorbent polymer. The water-soluble ethylenically unsaturated monomers which meet the description include carboxyl group-containing monomers such as (meth)acrylic acids and maleic acid, anhydrides thereof, and salts thereof; and sulfonic acid group-containing monomers such as 2-acrylamide-2-methylpropanesulfonic acid, 2-(meth) acryloyloxyethanesulfonicacids, 2-(meth)acryloyloxypropanesulfonic acids, vinylsulfonic acids and salts thereof, for example. Among other water-soluble ethylenically unsaturated monomers mentioned above, (meth)acrylic acids and salts thereof prove to be particularly desirable.

Optionally, the monomer may incorporate therein a cross-linking agent, a viscosity-adjusting agent, and other additives.

The cross-linking agents which are usable advantageously herein include polyfunctional ethylenically unsaturated monomers such as methylenebisacrylamide, ethylene glycol di(meth)acrylates, polyethylene glycol di(meth)acrylates, triallylamine, and trimethylolpropane triacrylate; polyglycidyl ethers such as ethylene glycol diglycidyl ether and polyethylene glycol diglycidyl ether; polyols such as glycerol and pentaerythritol; polyamines such as ethylene diamine and polyethylene imine; and compounds such as polyvalent metal salts represented by calcium chloride and aluminum sulfate which possess at least two functional groups capable of reacting with such functional groups as carboxyl group and sulfonic acid group, for example.

For the purpose of enhancing the efficiency of adhesion of the monomer to the fibrous web, it is permissible to use a viscosity-regulating agent such as methyl cellulose or hydroxyethyl cellulose. It is also permissible to use a filler such as ground pulp or short synthetic fibers and a foaming agent such as baking powder.

The adhesion of the monomer to the fibrous web can be attained by any of various known methods such as, for example, impregnating the fibrous web with the monomer or an aqueous solution of the monomer prepared by diluting the monomer with an aqueous liquid, applying the monomer to the fibrous web by screen printing or gravure printing or by roll coating or spray coating.

From the fibrous web having the monomer applied fast thereto, the absorbent composite (A) is obtained by converting the monomer into an absorbent polymer by polymerization of the known method. The absorbent polymer so obtained by polymerization of the monomer may be in the form of a homopolymer or a copolymer of the monomer or a polymer grafted as to cellulose, for example.

The polymerization may be effected through the agency of heat, light, ultraviolet light, or radiation, preferably in a polymerically inactive atmosphere such as, for example, in an atmosphere of nitrogen gas. Generally, in the polymerization with heat, the monomer is preferable to have a water-soluble radical initiator incorporated in advance therein. In the polymerization with light or ultraviolet light, it is preferable to have incorporated in advance therein a water-soluble photopolymerization initiator capable of generating a radical on exposure to light or ultraviolet light.

When the absorbent composite (A) is obtained by the use of an aqueous monomer solution, the absorbent composite (A) may be optionally treated with heating means such as hot air, microwave, or ultraviolet light to expel the water remaining after the polymerization by desiccation.

For the purpose of partially altering the absorbing ability of the produced absorbent composite (A), the aforementioned compound possessing at least two functional groups capable of reacting with a carboxyl group or sulfonic acid group may be partially added to the absorbent composite. The amount of the polymer thus formed is the range of 10 to 2,000 parts by weight, preferably 50 to 1,000 parts by weight, based on 100 parts by weight of the fibrous web.

The fibrous webs which are usable effectively in the absorbent composite (A) of the present invention include paper, ribbons, knit fabric, non-woven fabric, and woven fabric made of synthetic fibers such as polyester and polyolefins or cellulosic fibers such as cotton and pulp. Among other fibrous webs mentioned above, those made of polyester, polypropylene, and polyethylene prove to be particularly desirable. Optionally, a fibrous web having a desired pattern of dots, circles, rings, stripes, and checkers imparted therein by heat embossing may be used.

The term "powdery absorbent polymer (B)" as used in the present invention refers to the powder of a polymer possessing the nature of swelling by absorbing a large volume of an aqueous liquid and assuming the form of gel several times to several thousand times its own weight. Examples of the powdery absorbent polymer which answer this description include hydrolyzed starch-acrylonitrile graft polymer, neutralized starch-acrylic acid graft polymer, saponified vinyl acetate-acrylic acid ester copolymer, hydrolyzed acrylonitrile type copolymers or acrylamide type copolymers and cross-linked products of such copolymers, self-cross-linking type sodium polyacrylate obtained by reversed-phase suspension polymerization, and partially neutralized cross-linked polyacrylic acid invariably in the powdery form.

This invention does not discriminate the powdery absorbent polymer (B) by the shape of its particles. The particles of the powder may be in the form of spheres, scales, granules, and amorphous beads, for example. The size of these particles of the absorbent polymer (B) powder may be such that the powder may be fixed safely at a stated position in the absorbent member of the body fluid-absorbing article and fixed powder may refrain from imparting any unpleasant feeling to the user's skin. The particles of this powder are desired to have an average diameter in the range of 0.05 to 1.0 mm. If the average particle diameter is less than 0.05 mm, the work of fixing the powder at a stated position in the absorbent member during the production of the body fluid-absorbing article may possibly become difficult. Conversely, if the average particle diameter exceeds 1.0 mm, the powder is too coarse to impart a comfort to the user or to manifest desirable absorption characteristics. When a body fluid absorbing article is formed by depositing the powdery absorbent polymer (B) into the absorbent article with the absorbent composite (A), an amount of the powdery absorbent polymer (B) to be used is not more than 50 parts by weight, preferably in the range of 2 to 25 parts by weight, based on 100 parts by weight of the absorbent member.

The body fluid-absorbing article of this invention is characterized by causing the absorbent composite (A) obtained by the method described above to be deposited in half of the thickness of the absorbent member on the front-surface member side.

The body fluid-absorbing article of this invention is characterized by causing the absorbent composite (A) obtained by the method described above to be deposited in half of the thickness of the absorbent member on the front-surface member side and the absorbent polymer (B) in the powdery form to be deposited in half of the thickness of the absorbent member on the rear-surface member side.

The term "absorbent member" as used herein refers to the part of the body fluid-absorbing article which fulfils the function of absorbing and retaining body fluid. It is obtained by the conventional method of superposing fibrous absorbent layers of absorbent paper, non-woven fabric, or fibrous pulp. The absorbent member may be optionally subjected to an embossing or pressing treatment prior to actual use.

The present invention requires the aforementioned absorbent composite (A) to be contained in at least part of the absorbent member and more specifically disposed in half of the thickness of the absorbent member on the front surface member side. If the absorbent composite (A) is disposed in half of the thickness of the absorbent member on the rear-surface member side, it does not lend itself to enhancing the absorption characteristics of the body fluid-absorbing article. In the body fluid-absorbing article having the absorbent composite (A) disposed in half of the thickness of the absorbent member on the rear-surface member side instead on the front-surface member side, the body fluid is absorbed at a very low speed and the absorbed body fluid is retained with very poor power.

When the body fluid-absorbing article of this invention is constructed by incorporating in the absorbent member the powdery absorbent polymer (B) in addition to the absorbent composite (A), it is essential that the absorbent composite (A) should be disposed in half of the thickness of the absorbent member on the front-surface member side and, at the same time, the powdery absorbent polymer (B) should be disposed in half of the thickness of the absorbent member on the rear-surface member side.

If the absorbent composite (A) is disposed in half of the thickness of the absorbent member on the rear-surface member side or the powdery absorbent polymer (B) is disposed in half of the thickness of the absorbent member on the front-surface member side, they are not allowed to enhance the absorption characteristics of the body fluid-absorbing article. When the absorbent composite (A) is disposed in half of the thickness of the absorbent member not on the front-surface member side but on the rear-surface member side and the powdery absorbent polymer (B) is disposed in half of the thickness of the absorbent member not on the rear-surface member side but on the front-surface member side, the body fluid is absorbed at a very low speed and the absorbed body fluid is retained with very poor power.

Moreover, the powdery absorbent polymer disposed near the front-surface member side absorbs body fluid and converts itself into a soft gel and readily moves closely to the front-surface member and mars the shape of the absorbent member.

By causing the absorbent member obtained as described above to be interposed between the front-surface member permeable to body fluid and the rear-surface member (leakproof sheet) impervious to body fluid, the body fluid-absorbing article of this invention is produced.

As the front-surface member for use in this invention, any of the known liquid-permeables sheet materials which have been heretofore used in the conventional body fluid-absorbing articles on the side for contact with the user's body can be employed. For example, cloth or non-woven fabric made of such a fibrous material as polyester or rayon may be cited.

As the rear-surface member for use in the present invention, any of the known liquid-impermeable sheet materials heretofore used in the conventional body fluid-absorbing articles on the side exposed to contact with the user's outer garment may be employed. For example, a film of polyethylene or other similar plastic resin or a leakproofed fibrous sheet may be cited.

Now, the present invention will be described more specifically below with reference to working examples.

REFERENTIAL EXAMPLE 1

In 100 parts by weight of an aqueous monomer solution (monomer concentration 40% by weight) having the acrylic acid neutralized with sodium hydroxide (neutralization degree 75 mol %), 0.2 part by weight of 2,2'-azobis-N,N'-dimethyleneisobutylamidine hydrochloride and 0.005 part by weight of N,N'-methylenebisacrylamide were dissolved. The resultant aqueous monomer solution was bubbled with nitrogen gas to expel the dissolved oxygen therefrom. This aqueous monomer solution was applied in a rate of 250 g/m$^2$ by screen printing on a non-woven fabric of polypropylene having a basis weight of 30 g/m$^2$. The non-woven fabric having the aqueous monomer solution deposited fast thereon was held for 5 minutes between opposed iron sheet heated in advance to 80° C. to induce polymerization of the monomer. Then, the non-woven fabric now containing a polymer layer was dried for 5 minutes in a hot-air drier at 120° C., to afford an absorbent composite (1).

The absorbent composite (1) was found, by the method to be described hereinafter, to have an absorption capacity of 42 g/g.

METHOD FOR DETERMINATION OF ABSORPTION CAPACITY

About 0.5 g of a sample absorbent composite cut into minute fragments is placed in a teabag-like pouch of non-woven fabric (40 mm × 150 mm) and kept immersed for 30 minutes in an aqueous solution containing 0.9% by weight of sodium chloride. Then, the teabag-like pouch is removed from the aqueous solution, drained of excess aqueous solution for 5 minutes, and weighed. The absorption capacity of the sample absorbent composite is calculated in accordance with the following formula.

Absorption capacity (g/g)=[(weight of a sample teabag-like pouch after absorption) − (weight of a blank after absorption)]/(Weight of absorbent composite)

REFERENTIAL EXAMPLE 2

A non-woven fabric of polyester having a basis weight of 45 g/m$^2$ was immersed in the same aqueous monomer solution as used in Referential Example 1 until it was thoroughly impregnated with the aqueous monomer solution. It was squeezed to decrease the amount of the aqueous monomer solution adhering thereto to 300 g/m$^2$. Then, the non-woven fabric holding the aqueous monomer solution was left standing at 80° C. for 5 minutes to induce polymerization of the monomer and dried for 5 minutes in a hot-air drier at 120° C., to afford an absorbent composite (2).

The absorbent composite (2) thus obtained was found to have an absorption capacity of 43 g/g.

REFERENTIAL EXAMPLE 3

In 100 parts by weight of an aqueous 50 wt% monomer solution containing 20 mol% of acrylic acid, 60 mol% of potassium acrylate, and 20 mol% of potassium 2-methacryloylethane sulfonate, 0.5 part by weight of potassium persulfate, 0.003 part by weight of ethylene glycol diacrylate, and 0.1 part by weight of hydroxyethyl cellulose were dissolved. The resultant aqueous solution was bubbled with nitrogen gas to expel the dissolved oxygen therefrom. A non-woven fabric of polypropylene having a basis weight of 30 g/m$^2$ was immersed in the aqueous monomer solution until it was thoroughly impregnated with the aqueous monomer solution and then squeezed until the amount of the aqueous monomer solution adhering thereto decreased to 150 g/m$^2$. Then, the non-woven fabric holding the aqueous monomer solution was left standing at 80° C. for 3 minutes to induce polymerization of the monomer. It was further held for 30 seconds in a drier provided with a microwave generator of 600 W of output adapted to generate a microwave having a wavelength of 2,450 MHz. Consequently, there was obtained an absorbent composite (3).

This absorbent composite (3) was found to have an absorption capacity of 33 g/g.

EXAMPLE 1

On a square (10 cm × 10 cm) polyethylene film (having a basis weight of 18 g/m$^2$) as a body fluid-impermeable material, 3.5 g of fibrous pulp was evenly superposed and then the absorbent composite (1) obtained in Referential Example 1 cut in the shape of a square of 10 cm × 10 cm was superposed on the layer of the fibrous pulp. Further on the square absorbent composite (1), 1.5 g of fibrous pulp was superposed and finally a square (10 cm × 10 cm) non-woven fabric of polyester (having a basis weight of 20 g/m$^2$) as a body fluid-permeable front-surface material was superposed thereon, to afford a body fluid-absorbing article (1) conforming to the present invention.

The body fluid-absorbing article (1) thus obtained had an absorbent member composed of the fibrous pulp and the absorbent composite (1) and interposed between the front-surface member and the rear-surface member. The absorbent member had a thickness of 6 mm and the absorbent composite (1) was positioned 4 mm apart in the direction of thickness from the rear-surface member.

EXAMPLE 2

On the same rear-surface material of polyethylene film as used in example 1, 5.0 g of fibrous pulp was superposed and then 0.3 g of absorbent paper, one sheet of the absorbent composite (1) obtained in Referential Example 1, and 0.3 g of absorbent paper invariably cut in the shape of a square of 10 cm × 10 cm were superposed sequentially in the order mentioned so that the absorbent composite (1) would be interposed between the two absorbent papers, and finally the same non-woven fabric of polyester as used in Example 1 was superposed as a front-surface material, to afford a body fluid-absorbing article (2) conforming with this invention.

The body fluid-absorbing article (2) thus obtained had the absorbent member composed of the fibrous pulp, the absorbent papers, and the absorbent composite (1) and interposed between the front-surface member and the rear-surface member. The absorbent member had a thickness of 6.4 mm and the absorbent composite (1) was positioned 5.6 mm apart in the direction of thickness from the rear-surface member.

EXAMPLE 3

A body fluid-absorbing article (3) was obtained by following the procedure of Example 1, except that the absorbent composite (2) obtained in Referential Example 2 was used in the place of the absorbent composite (1). In the produced body fluid-absorbing article (3), the absorbent member had the same thickness and the absorbent composite (2) was positioned at the same depth as in the body fluid-absorbing article (1).

EXAMPLE 4

A body fluid-absorbing article (4) was obtained by following the procedure of Example 2, except that the absorbent composite (2) obtained in Referential Example 2 was used in the place of the absorbent composite (1). In the produced body fluid-absorbing article (4), the absorbent member had the same thickness and the absorbent composite (2) was positioned at the same depth as in the body fluid-absorbing article (2).

EXAMPLE 5

A body fluid-absorbing article (5) was obtained by following the procedure of Example 1, except that the absorbent composite (3) obtained in Referential Example 3 was used in the place of the absorbent composite (1). In the produced body fluid-absorbing article (5), the absorbent member had the same thickness and the absorbent composite (3) was positioned at the same depth as in the body fluid-absorbing article (1).

CONTROL 1

On the same rear-surface material of polyethylene film as used in Example 1, 1.5 g of fibrous pulp was superposed, then one sheet of a square (10 cm × 10 cm) of the absorbent composite (1) obtained in Referential Example 1 was superposed thereon, 3.5 g of fibrous pulp was superposed thereon, and finally the same non-woven fabric of polyester as used in Example 1 was further superposed as a front-surface material, to afford a body fluid-absorbing article (1) for comparison.

The body fluid-absorbing article (1) for comparison thus obtained had the absorbent member composed of the fibrous pulp and the absorbent composite (1) and interposed between the front-surface member and the rear-surface member. The absorbent member had a thickness of 6 mm and the absorbent composite (1) was positioned 2 mm away in the direction of thickness from the rear-surface member.

CONTROL 2

On the same rear-surface material of polyethylene film as used in Example 1, 0.3 g of absorbent paper, one sheet of the absorbent composite (1) obtained in Referential Example 1, and 0.3 g of absorbent paper invariably cut in the shape of a square of 10 cm × 10 cm were sequentially superposed in the order mentioned so as to have the absorbent composite (1) interposed between the absorbent papers and then 5.0 g of fibrous pulp was superposed thereon and finally the same non-woven fabric of polyester as used in Example 1 was superposed as a front-surface material, to afford a body fluid-absorbing article (2) for comparison.

The body fluid-absorbing article (2) for comparison consequently obtained had the absorbent member composed of the fibrous pulp, the absorbent paper, and the absorbent composite (1) and interposed between the front-surface member and the rear-surface member. The absorbent member had a thickness of 6.4 mm and the absorbent composite (1) was positioned 0.8 mm away in the direction of thickness from the rear-surface member.

CONTROL 3

A body fluid-absorbing article (3) for comparison was obtained by following the procedure of Control 1, except that the absorbent composite (2) obtained in Referential Example 2 was used in the place of the absorbent composite (1). In the body fluid-absorbing article (3) for comparison, the absorbent member had the same thickness and the absorbent composite (2) was positioned at the same depth as in the body fluid-absorbing article (1) for comparison.

CONTROL 4

A body fluid-absorbing article (4) for comparison was obtained by following the procedure of Control 2, except that the absorbent composite (2) obtained in Referential Example 2 was used in the place of the absorbent composite (1).

In the body fluid-absorbing article (4) for comparison, the absorbent member had the same thickness and the absorbent composite (2) was positioned at the same depth as in the body fluid-absorbing article (2) for comparison.

EXAMPLE 6

The body fluid-absorbing articles (1) to (5) and the body fluid-absorbing articles (1) to (4) for comparison obtained respectively in Examples 1 to 5 and Controls 1 to 4 were tested for absorption characteristics (absorption speed and power of retaining absorbed body fluid) by the methods to be described hereinafter. The results are shown in Table 1.

METHOD FOR EVALUATION OF ABSORPTION CHARACTERISTICS (a) Speed of absorption

Onto the central part of a sample body fluid-absorbing article spread with the rear-surface member on the lower side on a horizontal table, 50 cc of artificial urine (water containing 0.8% of sodium chloride, 0.1% of calcium chloride, 0.1% of magnesium sulfate, and 1.9% of urea) is poured and left standing until complete disappearance due to absorption. The time of this standing is clocked and reported.

(b) Power to retain artificial urine

The sample body fluid-absorbing article used in the test for speed of absorption is left standing for 20 minutes on the horizontal table. Then, a paper towel is placed on the front-surface member of the body fluid-absorbing article and pressed under a load of 40 g/cm$^2$. The amount of artificial urine absorbed by the paper towel for one minute (amount of backflow) is measured and reported as the power to hold artificial urine.

The amount of backflow has a meaning such that the magnitude of the power to retain artificial urine decreases in proportion as the value of this amount increases.

TABLE 1

| Body fluid-absorbing article used for evaluation of absorption characteristics | Results of evaluation of characteristics | |
|---|---|---|
| | Speed of absorption (sec) | Power to retain absorbed urine (amount of backflow in g) |
| Body fluid-absorbing article (1) | 10 | 5.2 |
| Body fluid-absorbing article (2) | 8 | 5.4 |
| Body fluid-absorbing article (3) | 7 | 4.9 |
| Body fluid-absorbing article (4) | 8 | 4.1 |
| Body fluid-absorbing article (5) | 9 | 6.1 |
| Body fluid-absorbing article for comparison (1) | 16 | 9.8 |
| Body fluid-absorbing article for comparison (2) | 17 | 10.4 |
| Body fluid-absorbing article for comparison (3) | 17 | 11.2 |
| Body fluid-absorbing article for comparison (4) | 16 | 11.0 |

EXAMPLE 7

On a square (10 cm × 10 cm) polyethylene film (having a basis weight of 18 g/m$^2$) as a rear-surface material impervious to body fluid, 1.5 g of fibrous pulp was superposed evenly, 0.3 g of a powdery absorbent polymer of a partially neutralized cross-linked polyacrylic acid having an average particle diameter of 0.3 mm (produced by Nippon Shokubai Kagaku Kogyo Co., Ltd. and marketed under trademark designation of "Aqualic CA") was sprayed thereon and 1.5 g of fibrous pulp was superposed thereon and subsequently the absorbent composite (1) obtained in Referential Example 1 cut in the shape of a square 10 cm × 10 cm was superposed. Further, 1.5 g of fibrous pulp was superposed and finally a square (10 cm × 10 cm) non-woven fabric of polyester (having a basis weight of 20 g/m$^2$) was superposed thereon as a front-surface material, to afford a body fluid-absorbing article (6) conforming with the present invention.

The body fluid-absorbing article (6) thus obtained had the absorbent member composed of the fibrous pulp, the powdery absorbent polymer, and the absorbent composite (1) and interposed between the front-surface member and the rear-surface member. The absorbent member had a thickness of 5.4 mm and the powdery absorbent polymer was placed 1.3 mm away in the direction of thickness from the rear-surface member, and the absorbent composite (1) was positioned 3.4 mm away in the direction of thickness from the rear-surface member.

EXAMPLE 8

On the same rear-surface material of polyethylene film as used in Example 7, 2.3 g of fibrous pulp was superposed, 0.3 g of the same powdery absorbent polymer as used in Example 7 was sprayed thereon, then 2.3 g of fibrous pulp was superposed, then 0.3 g of absorbent paper, the absorbent composite (1) obtained in Referential Example 1, and 0.3 g of absorbent paper invariably cut in the shape of a square 10 cm × 10 cm were superposed, and finally the same non-woven fabric of polyester as used in Example 7 was superposed as a front-surface material, to afford a body fluid-absorbing article (7) conforming with the present invention.

The body fluid-absorbing article (7) thus obtained had the absorbent member composed of the fibrous pulp, the absorbent paper, the powdery absorbent polymer, and the absorbent composite (1) and interposed between the front-surface member and the rear-surface member. The absorbent member had a thickness of 5.6 mm and the powdery absorbent polymer was positioned 2.0 mm away in the direction of thickness from the rear-surface member and the absorbent composite (1) was positioned 4.8 mm away in the direction of thickness from the rear-surface member.

EXAMPLE 9

A body fluid-absorbing article (8) was obtained by following the procedure of Example 7, except that the absorbent composite (2) obtained in Referential Example 2 was used in the place of the absorbent composite (1) and a neutralized starch-acrylic acid graft polymer having an average particle diameter of 0.3 mm (produced by Sanyo Chemical Industry Co., Ltd. and marketed under trademark designation of "Sunwet IM2800") was used as a powdery absorbent polymer. In the body fluid-absorbing article (8), the absorbent member had the same thickness and the powdery absorbent polymer and the absorbent composite (2) were positioned at the same depths as in the body fluid-absorbing article (6).

EXAMPLE 10

A body fluid-absorbing article (9) was obtained by following the procedure of Example 8, except that the absorbent composite (2) obtained in Referential Example 2 was used in the place of the absorbent composite (1) and a neutralized starch-acrylic acid graft polymer having an average particle diameter of 0.3 mm (produced by Sanyo Chemical Industry Co., Ltd. and marketed under trademark designation of "Sunwet IM2800") was used as a powdery absorbent polymer. In the body fluid-absorbing article (9), the absorbent member had the same thickness and the powdery absorbent polymer and the absorbent composite (2) were positioned at the same depths as in the body fluid-absorbing article (7).

EXAMPLE 11

A body fluid-absorbing article (10) was obtained by following the procedure of example 7, except that the absorbent composite (3) obtained in referential example 3 was used in the place of the absorbent composite (1). In the body fluid-absorbing article (10), the absorbent member had the same thickness and the powdery absorbent polymer and the absorbent composite (3) were positioned at the same depths as in the body fluid-absorbing article (6).

EXAMPLE 12

A body fluid-absorbing article (11) was obtained by following the procedure of Example 7, except that the powder obtained by classifying the same powder (Aqualic CA) as used in Example 7 and collecting the fraction of an average particle diameter of 0.5 mm was used as a powdery absorbent polymer. In the body fluid-absorbing article (11), the absorbent member had the same thickness and the powdery absorbent polymer and the absorbent composite (1) were positioned at the same depths as in the body fluid-absorbing article (6).

EXAMPLE 13

A body fluid-absorbing article (12) was obtained by following the procedure of Example 7, excepting a powdery absorbent polymer having an average particle diameter of 0.1 mm (produced by Seitetsu Kagaku Co., Ltd. and marketed under trademark desigantion of "Acquakeep") was used in the place of Aqualic CA as powdery absorbent polymer. In the body fluid-absorbing article (12), the absorbent member had the same thickness and the powdery absorbent polymer and the absorbent composite (1) were positioned at the same depths as in the body fluid-absorbing article (6).

CONTROL 5

On the same rear-surface material of polyethylene film as used in Example 7, 1.5 g of fibrous pulp was superposed and then the absorbent composite (1) obtained in Referential Example 1 cut in the shape of a square 10 cm × 10 cm was superposed. Further, 1.5 g of fibrous pulp was superposed, 0.3 g of the same powdery absorbent polymer as used in Example 7 was sprayed therein, 1.5 g of fibrous pulp was superposed, and finally the same non-woven fabric of polyester as used in Example 7 was superposed as a front-surface material, to afford a body fluid-absorbing article (5) for comparison.

The body fluid-absorbing article (5) for comparison thus obtained had the absorbent member composed of the fibrous pulp, the powdery absorbent polymer, and the absorbent composite (1) and interposed between the front-surface member and the rear-surface member. The absorbent member had a thickness of 5.4 mm and the powdery absorbent polymer was positioned 4.1 mm away in the direction of thickness form the rear-surface member, and the absorbent composite (1) was positioned 2.0 mm away in the direction of thickness from the rear-surface member.

CONTROL 6

On the same rear-surface material of polyethylene film as used in Example 7, 0.3 g of absorbent paper, the absorbent composite (1) obtained in Referential Example 1, and 0.3 g of absorbent paper invariably cut int he shape of a square 10 cm ×10 cm were superposed sequentially in the order mentioned so as to have the absorbent composite (1) interposed between the absorbent papers. Then, 2.3 g of fibrous pulp was superposed thereon, 0.3 g of the same powdery absorbent polymer as used in Example 7 was sprayed, and 2.3 g of fibrous pulp was superposed, and finally the same non-woven fabric of polyester as used in Example 7 was superposed as a front-surface material, to afford a body fluid-absorbing article (6) for comparison.

The body fluid-absorbing article (6) for comparison thus obtained had the absorbent member composed of the fibrous pulp, the absorbent paper, the powdery absorbent polymer, and the absorbent composite (1) and interposed between the front-surface member and the rear-surface member. The absorbent member had a thickness of 5.6 mm and the powdery absorbent polymer was positioned 3.6 mm away in the direction of thickness from the rear-surface member and the absorbent composite (1) was positioned 0.8 mm away in the direction of thickness from the rear-surface member.

A body fluid-absorbing article (7) for comparison was obtained by following the procedure of Control 5, excepting the absorbent composite (2) obtained in Referential Example 2 was used in the place of the absorbent composite (1) and a neutralized starch-acrylic acid graft polymer having an average particle diameter of 0.3 mm (produced by Sanyo Chemical Industry Co., Ltd. and marketed under trademark designation of "Sunwet IM2800") was used as a powdery absorbent polymer. In the body fluid-absorbing article (7) for comparison, the absorbent member had the same thickness and the powdery absorbent polymer and the absorbent composite (2) were positioned at the same depths as in the body fluid-absorbing article (5) for comparison.

CONTROL 8

A body fluid-absorbing article (8) for comparison was obtained by following the procedure of Control 6, excepting the absorbent composite (2) obtained in Referential Example 2 was used in the place of the absorbent composite (1) and a neutralized starch-acrylic acid graft polymer having an average particle diameter of 0.3 mm (produced by Sanyo Chemical Industry Co., Ltd. and marketed under trademark designation of "Sunwet IM2800") was used as a powdery absorbent polymer. In the body fluid-absorbing article (8) for comparison, the absorbent member had the same thickness and the powdery absorbent polymer and the absorbent composite (2) were positioned at the same depths as in the body fluid-absorbing article (6) for comparison.

EXAMPLE 14

The body fluid-absorbing article (6) to (12) conforming with this invention and the body fluid-absorbing articles (5) to (8) for comparison obtained respectively in Examples 7 to 13 and Controls 5 to 8 were tested for absorption characteristics (speed of absorption and powder to retain absorbed body fluid) by the method described in Example 6. The results are shown in Table 2.

TABLE 2

| Body fluid-absorbing article used for evaluation of absorption characteristics | Results of evaluation of characteristics | |
|---|---|---|
| | Speed of absorption (sec) | Power to retain absorbed urine (amount of backflow in g) |
| Body fluid-absorbing article (6) | 9 | 2.1 |
| Body fluid-absorbing article (7) | 8 | 1.9 |
| Body fluid-absorbing article (8) | 8 | 2.2 |
| Body fluid-absorbing article (9) | 7 | 2.0 |
| Body fluid-absorbing article (10) | 8 | 2.9 |
| Body fluid-absorbing article (11) | 7 | 1.8 |

TABLE 2-continued

| Body fluid-absorbing article used for evaluation of absorption characteristics | Results of evaluation of characteristics | |
|---|---|---|
| | Speed of absorption (sec) | Power to retain absorbed urine (amount of backflow in g) |
| Body fluid-absorbing article (12) | 10 | 2.5 |
| Body fluid-absorbing article for comparison (5) | 18 | 7.0 |
| Body fluid-absorbing article for comparison (6) | 20 | 7.2 |
| Body fluid-absorbing article for comparison (7) | 20 | 7.2 |
| Body fluid-absorbing article for comparison (8) | 19 | 7.7 |

What is claimed is:

1. In a body fluid-absorbing article composed of a liquid-permeable front-surface member, a liquid impermeable, rear-surface member and a fibrous absorbent member nipped therebetween and adopted to be used with said front-surface member held in contact with the human body, by the improvement having disposed substantially only in the half of the thickness of said absorbent member on the front-surface member side an absorbent composite (a) obtained by applying an ethylenically unsaturated monomer capable of forming an absorbent polymer by polymerization of an aqueous solution of said monomer to a fibrous web and thereafter polymerizing the monomer, provided said absorbent composite is out of contact with said front surface member.

2. An article according to claim 1, wherein said ethylenically unsaturated monomer is at least one member selected from the group consisting of carboxyl group-containing monomers, sulfonic acid group-containing monomers, and salts thereof.

3. An article according to claim 1, wherein said absorbent member comprises said absorbent composite (A) and a fibrous absorbent material.

4. An article according to claim 3, wherein said fibrous absorbent material is at least one member selected from the group consisting of fibrous pulp and absorbent paper.

5. An article according to claim 2, wherein said carboxyl group-containing monomer or a salt thereof is at least one member selected from the group consisting of acrylic acid, methacrylic acid, maleic aid, maleic anhydride, and salts thereof.

6. An article according to claim 2, wherein said carboxyl group-containing monomer or a salt thereof is at least one member selected from the group consisting of acrylic acid, methacrylic acid, and salts thereof.

7. An article according to claim 2, wherein said sulfonic acid group-containing monomer or a salt thereof is at least one member selected from the group consisting of 2-acrylamide-2-methylpropanesulfonic acid, 2-(meth)acryloyloxyethanesulfonic acid, 2-(meth)acryloyloxypropanesulfonic acid, vinylsulfonic acids, and salts thereof.

8. In a body fluid-absorbing article composed of a liquid-permeable front-surface member, a liquid-impermeable rear-surface member, and a fibrous absorbent member nipped therebetween and adapted to be used with said front-surface member held in contact with the human body, by the improvement having disposed substantially only in the half of the thickness of said absorbent member on the front-surface member side an absorbent composite (A) obtained by applying an ethylenically unsaturated monomer capable of forming an absorbent polymer by polymerization of an aqueous solution of said monomer to a fibrous web and thereafter polymerizing the monomer, and having disposed substantially only in the half of the thickness of said absorbent member on the rear-surface member side a powdery absorbent polymer (B), provided said absorbent composite is out of contact with said front surface member and said powdery absorbent polymer is out of contact with said rear surface member.

9. An article according to claim 8, wherein said ethylenically unsaturated monomer is at least one member selected from the group consisting of carboxyl group-containing monomers, sulfonic acid group-containing monomers, and salts thereof.

10. An article according to claim 8, wherein said absorbent member comprises said absorbent composite (A), said powdery absorbent polymer (B) and a fibrous absorbent material.

11. An article according to claim 10, wherein said fibrous absorbent material is at least one member selected from the group consisting of fibrous pulp and absorbent paper.

12. An article according to claim 9, wherein said carboxyl group-containing monomer or a salt thereof is at least one member selected from the group consisting of acrylic acid, methacrylic acid, maleic acid, maleic anhydride, and salts thereof.

13. An article according to claim 9, wherein said carboxyl group-containing monomer or a salt thereof is at least one member selected from the group consisting of acrylic acid, methacrylic acid, and salts thereof.

14. An article according to claim 9, wherein said sulfonic acid group-containing monomer or a salt thereof is at least one member selected from the group consisting of 2-acrylamide-2-methylpropanesulfonic acid, 2-(meth)acryloyloxyethanesulfonic acid, 2-(meth)acryloyloxypropanesulfonic acid, vinylsulfonic acids, and salts thereof.

15. An article according to claim 8, wherein an average particle size of said absorbent polymer (B) is in the range of 0.05 to 1.0 mm.

* * * * *